United States Patent [19]

Holtkamp, Sr.

[11] Patent Number: Plant 7,056

[45] Date of Patent: Nov. 14, 1989

[54] AFRICAN VIOLET PLANT NAME WEST VIRGINIA

[76] Inventor: Reinhold Holtkamp, Sr., Werther Strasse 112, D4294 Isselburg, Fed. Rep. of Germany

[21] Appl. No.: 262,578

[22] Filed: Oct. 26, 1988

[51] Int. Cl.[4] ..... A01H 5/00

[52] U.S. Cl. ..... Plt./69

[58] Field of Search ..... Plt./69

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct cultivar of African violet named West Virginia characterized by its single, pink, wavy and frilled flowers with darker center radiating irregularly into the 2 small petals; dark pink line on the edges, especially of the two small petals; strong, upright flower stems that curve toward the center to form a compact bouquet above the leaves; dark green slightly serrated leaves, profuse flowering, vigorous growth habit, flowering 10–11 weeks after potting, and its long lasting and non-dropping flowers.

1 Drawing Sheet

The present invention comprises a new and distinct cultivar of African violet plant, botanically known as *Saintpaulia ionantha*, and hereinafter referred to by the cultivar name West Virginia.

The new cultivar was referred to during the breeding and selection process by the designation G 20/VIII and is a product of a planned breeding program. The new cultivar was originated from a cross made by me in the controlled breeding program in Haffen, Federal Republic of Germany. The female, or seed parent was a cultivar designated d 150/4. The male, or pollen parent was a cultivar designated d 150.1.

West Virginia was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of a sexual reproduction.

West Virginia has not been observed under all possible environmental conditions. The phenotype may vary significantly with variations in environment such as temperature, light intensity and day length. The following observations, measurements and values describe the new cultivar as grown in a 10 cm pot in Haffen, West Germany and Nashville, Tenn. under greenhouse conditions which closely approximate those generally used in commercial practice.

The following traits have been repeatedly observed and are determined to be basic characteristics of West Virginia, which in combination distinguish this African violet as a new and distinct cultivar:

(1) Strong, upright flower stems curving slightly toward the center.

(2) Single pink flowers with a darker center radiating irregularly into the two small petals and with frilled and wavy edges that have a dark line.

(3) Profuse flowering.

(4) Each plant has 7–8 and more upright flower stems each of which carries 6–8 and more flowers.

(5) Long lasting, non-dropping flowers.

(6) Vigorous grower.

(7) Plant saleable 10 to 11 weeks after potting.

(8) Seed capsules push slightly through.

(9) Dark green leaves.

(10) After maturity the flowers dry off and remain on the peduncle without becoming infected by botrytis.

The closest known variety is Farrah, whose leaf color and flower shape and flower color are similar to West Virginia. Differences between Farrah and West Virigina are the lighter pink color, the frilled edges and the dark line on the edge of the flowers of West Virginia.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 2 p.m. in Nashville, Tenn.

Botanical Classification: *Saintpaulia ionantha,* Ramat., c.v. West Virginia.

Parentage:

*Male parent.*—d 150/1.

*Female parent.*—d 150/4.

Propagation: The new cultivar holds its distinguishing characteristics through successive propagations by leaf cuttings.

Plant: From 10 cm to 12 cm tall when grown in pots, and approximately 24–26 cm in diameter when fully grown.

*Leaves.*—General form: Oval to heart-shaped. Diameter: 60–75 mm. Texture: Velvety. Aspect: Shiny, hairy, slightly serrated. Veins: Upperside: visible; underside: very well pronounced, light green, shiny. Color (upperside): Yellow-green group 147 A and darker. Color (underside): Greyed-purple group 186 B; older leaves Greyed-green group 194 D with touch of Greyed-Purple Group 186 B. Petiole: Strong upright, purplish green, hairy.

*Flowers.*—Buds: Ball-shaped, 7–9 mm just before opening, purplish pink. Sepals: Five (5). Color: Green with purplish brown touch. Calyx: Shape:

Funnel-shaped. Aspect: Spear-shaped, hairy. Peduncle: Character: Strong upright, hairy. Color: Purplish brown. Individual flowers: Size: 40–45 mm. Shape: Single violet-shaped (3 large and 2 small petals) with frilled and wavy edges. Color (upperside): Red-Purple Group 74 between C and D and lighter. Under cooler temperatures and more intensive lighting, the pink tends to intensify. Color (underside): Red-Purple Group 74 D and lighter. Borne: Each flower stem carries 6–8 and more flowers on strong, upright peduncle that are free standing above the leaves, thereby forming a compact bouquet. Flowering habit: Flowers 10–11 weeks after potting.

*Reproductive organs.*—Stamens: Two (2). Anthers: 2 composed of 4 anther cells, seed capsule pushes slightly through. Filaments: Yellowish green with pink touch on edges, 4 mm long. Pollen color: Yellow Group 7 A. Styles: 7 mm long, dark pink; base of ovary light green and hairy.

*Roots.*—Normally developed, white when young, turning slightly brownish when older.

Disease resistance: Good.

General observations: West Virginia is a very attractive, vigorous grower with dark green, velvety and shiny leaves. A tight bouquet of single violet-shaped flowers free standing above the leaves develops after approximately 10–11 weeks. Each of the 7–8 and more strong flower stems carries 6–8 and more single, pink, wavy and frilled flowers. The pink color in the center is darker and radiates irregularly into the petals, especially the two small ones. The edges of the petals, especially of the two small ones, have a dark line. Occasionally, 1–2 additional small petals may develop. The flowers are long-lasting and non-dropping.

I claim:

1. A new and distinct cultivar of African violet named West Virginia, as described and illustrated, and particularly characterized by its single, pink, wavy and frilled flowers with darker center radiating irregularly into the 2 small petals; dark pink line on the edges, especially of the two small petals; strong, upright flower stems that curve toward the center to form a compact bouquet above the leaves; dark green slightly serrated leaves, profuse flowering, vigorous growth habit, flowering 10–11 weeks after potting, and its long lasting and non-dropping flowers.

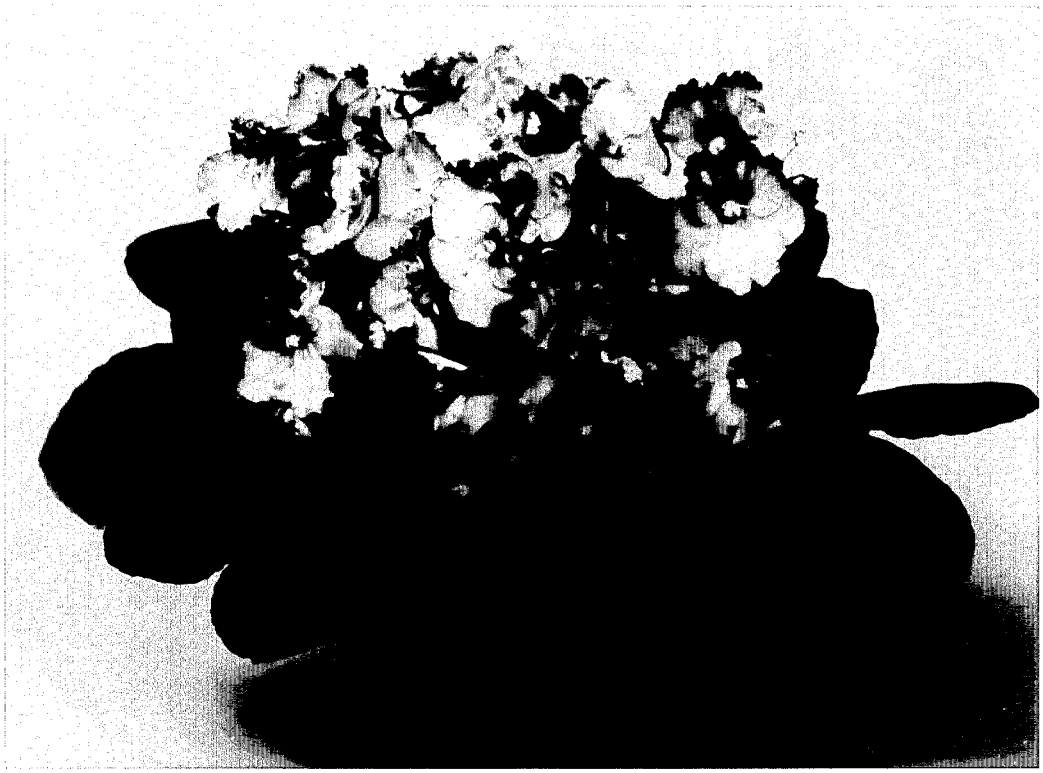

* * * * *